(12) United States Patent
McCall et al.

(10) Patent No.: US 9,818,157 B2
(45) Date of Patent: Nov. 14, 2017

(54) METHOD FOR USING ELECTRONIC METADATA TO VERIFY INSURANCE CLAIMS

(75) Inventors: Thomas A. McCall, Frisco, TX (US); William D. Bryant, Mount Pleasant, SC (US); John W. S. Riney, Ladson, SC (US); Christopher E. Gay, Dallas, TX (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 952 days.

(21) Appl. No.: 12/365,047

(22) Filed: Feb. 3, 2009

(65) Prior Publication Data

US 2010/0088123 A1 Apr. 8, 2010

Related U.S. Application Data

(60) Provisional application No. 61/103,363, filed on Oct. 7, 2008.

(51) Int. Cl.
| | |
|---|---|
| G06Q 40/00 | (2012.01) |
| G06Q 40/08 | (2012.01) |
| G06Q 20/32 | (2012.01) |
| G06F 19/00 | (2011.01) |
| G06Q 30/06 | (2012.01) |
| G06Q 50/22 | (2012.01) |
| G06Q 20/38 | (2012.01) |

(Continued)

(52) U.S. Cl.
CPC ......... *G06Q 40/08* (2013.01); *G06Q 20/3276* (2013.01); *G06F 19/321* (2013.01); *G06F 19/322* (2013.01); *G06F 19/327* (2013.01); *G06F 19/328* (2013.01); *G06Q 10/101* (2013.01); *G06Q 20/387* (2013.01); *G06Q 30/02* (2013.01); *G06Q 30/06* (2013.01); *G06Q 40/00* (2013.01); *G06Q 50/22* (2013.01)

(58) Field of Classification Search
CPC ........ G06Q 40/00; G06Q 40/08; G06Q 50/22; G06Q 20/3276; G06Q 30/02; G06Q 30/06; G06Q 10/101; G06Q 20/387; G06F 19/322; G06F 19/327; G06F 19/328; G06F 19/321
USPC ...................................... 705/4, 35
See application file for complete search history.

(56) References Cited

U.S. PATENT DOCUMENTS

| | | |
|---|---|---|
| 5,797,134 A | 8/1998 | McMillan et al. |
| 6,064,970 A | 5/2000 | McMillan et al. |

(Continued)

OTHER PUBLICATIONS

Captiva and quickstream form strategic alliance and integrate products; first customer roll-out underway. (May 6, 2002). Business Wire Retrieved from https://dialog.proquest.com/professional/professional/docview/678900894?accountid=142257 on Jun. 27, 2017.*

(Continued)

*Primary Examiner* — Kito R Robinson
(74) *Attorney, Agent, or Firm* — Marshall, Gerstein & Borun LLP; Randall G. Rueth

(57) ABSTRACT

A method includes receiving a digital file from a customer, extracting metadata from the file, and verifying the metadata prior to accepting the digital file. The method may include verifying that a representation of a required physical token appears in the digital file.

16 Claims, 2 Drawing Sheets

(51) Int. Cl.
 *G06Q 30/02* (2012.01)
 *G06Q 10/10* (2012.01)

(56) References Cited

U.S. PATENT DOCUMENTS

| | | | | |
|---|---|---|---|---|
| 6,873,336 | B1* | 3/2005 | Sailus | G06Q 30/02 345/581 |
| 6,995,789 | B2* | 2/2006 | McIntyre | G06Q 30/06 348/207.1 |
| 7,243,153 | B2* | 7/2007 | McIntyre | G06Q 30/06 709/229 |
| 7,398,319 | B2* | 7/2008 | McIntyre | G06Q 30/06 709/223 |
| 7,467,160 | B2* | 12/2008 | McIntyre | G06Q 20/387 |
| 7,809,587 | B2* | 10/2010 | Dorai et al. | 705/4 |
| 7,895,445 | B1* | 2/2011 | Albanese | G06F 21/335 713/172 |
| 8,019,629 | B1* | 9/2011 | Medina et al. | 705/4 |
| 8,412,837 | B1* | 4/2013 | Emigh | H04L 9/30 705/65 |
| 8,625,866 | B2* | 1/2014 | Hill | G06F 19/321 382/128 |
| 2001/0044733 | A1 | 11/2001 | Lee et al. | |
| 2002/0196344 | A1* | 12/2002 | McIntyre | G06Q 30/06 348/207.1 |
| 2003/0007200 | A1* | 1/2003 | McIntyre | G06Q 20/387 358/527 |
| 2003/0009469 | A1* | 1/2003 | Platt | G06F 17/30038 |
| 2003/0009527 | A1* | 1/2003 | McIntyre | G06F 17/30247 709/206 |
| 2003/0009569 | A1* | 1/2003 | McIntyre | G06Q 30/06 709/229 |
| 2003/0033173 | A1 | 2/2003 | Suzuki et al. | |
| 2003/0236686 | A1 | 12/2003 | Matsumoto et al. | |
| 2004/0218785 | A1 | 11/2004 | Kim | |
| 2005/0071283 | A1* | 3/2005 | Randle | G06Q 20/04 705/75 |
| 2005/0108540 | A1* | 5/2005 | Kusnoto | G06F 21/6209 713/176 |
| 2006/0026127 | A1* | 2/2006 | Bodlaender | G06F 17/30265 |
| 2006/0095301 | A1* | 5/2006 | Gay | 705/4 |
| 2006/0132291 | A1* | 6/2006 | Dourney et al. | 340/286.01 |
| 2006/0200582 | A1 | 9/2006 | Phipps | |
| 2006/0224964 | A1* | 10/2006 | Schwartz | G06F 17/30056 715/730 |
| 2007/0198287 | A1* | 8/2007 | Outwater | 705/1 |
| 2007/0214185 | A1* | 9/2007 | Fujiwara | G06F 17/30011 |
| 2007/0266252 | A1 | 11/2007 | Davis et al. | |
| 2008/0059348 | A1* | 3/2008 | Glassman | G06Q 30/02 705/35 |
| 2008/0109543 | A1* | 5/2008 | Abanami | G06F 21/10 709/223 |
| 2008/0184272 | A1* | 7/2008 | Brownewell | 719/318 |
| 2008/0191909 | A1 | 8/2008 | Mak | |
| 2009/0106052 | A1* | 4/2009 | Moldovan | G06Q 10/10 705/4 |
| 2009/0186603 | A1* | 7/2009 | Usami | H04M 1/274516 455/414.2 |
| 2009/0265385 | A1* | 10/2009 | Beland et al. | 707/104.1 |
| 2010/0046748 | A1* | 2/2010 | Kusnoto | G06F 21/6209 380/42 |
| 2010/0088123 | A1* | 4/2010 | McCall | G06Q 40/08 705/4 |
| 2010/0142769 | A1* | 6/2010 | Hirota | G06F 17/30271 382/118 |
| 2011/0176712 | A1* | 7/2011 | Hill | G06F 19/321 382/128 |

OTHER PUBLICATIONS

Dekeyser, S. (2005). A metadata collection technique for documents in WinFS. Paper presented at the 87. Retrieved from https://dialog.proquest.com/professional/professional/docview/1283932057?accountid=142257 on Jun. 27, 2017.*

Author Unknown, "2003 Best's Insurance Reports—Property/Casualty," *AM Best 2003 Edition*.

Anastasiadis, Stephanos, "Reconciling Environmental and Social Transport Policies," 2004, Publisher: T&E European Federation for Transport and Environment.

Author Unknown, "Consumer advocates question offering insurance at kiosks," 2004, Published at: www.atmmarketplace.com/news_printable.htm?id+14380.

Brady, Jeff, "Groups Propose Mileage-Based Car Insurance," *OPB News*, Dec. 13, 2002, Publisher: Oregon Public Broadcasting.

Braun, Thomas A., "Hit From Behind," *Best's Review*, Oct. 2002, pp. 59-61.

Butler, Patrick, "An Alternative to the High-Risk-Driver Theory: Adverse Selection Induced by Per-Car Premiums," Aug. 7, 2004, pp. 1-24, Publisher: Annual Meeting of the American Risk & Insurance Association in Chicago.

Butler, Patrick, "Cost-Based Pricing of Individual Automobile Risk Transfer: Car-Mile Exposure Unit Analysis," *Journal of Actuarial Practice*, 1993, pp. 51-84, vol. 1, No. 1, Publisher: Absalom Press.

Butler, Patrick, "Discussion of the paper 'On the Use of Accident or Conviction Counts to Trigger Action'," *Transportation Research Board*, 1993.

Butler, Patrick, "Discussion of Robert L. Brown's 'Recent Canadian Human Rights Decisions Having an Impact on Gender-Based Risk Classification Systems,'" *Journal of Actuarial Practice*, 1995, pp. 181-190, vol. 3, No. 1.

Butler, Patrick et al., "Driver Record: a Political Red Herring that Reveals the Basic Flaw in Automobile Insurance Pricing," *Journal of Insurance Regulation*, Dec. 1989, vol. 8, No. 2, Publisher: National Association of Insurance Commissioners.

Butler, Patrick, "Are Low-Income Drivers High Risk—or Victims of Adverse Selection Induced by Pay-per-Car Premiums?" Jan. 2004, pp. 1-14, Publisher: Annual Meeting of Western Risk & Insurance Association.

Butler, Patrick, "Automobile Insurance Pricing: Operating Cost versus Ownership Cost; the Implications for Women," *Proceedings of the 2nd National Conference on Women's Travel Issues*, 1996, Publisher: National Organization for Women.

Butler, Patrick, "Operation of an Audited-Mile/Year Auto Insurance System Under Pennsylvania Law," *The Casualty Actuarial Society Forum*, Jun. 22, 1992.

Butler, Patrick et al., "Sex-Divided Mileage, Accident, and Insurance Cost Data Show that Auto Insurers Overcharge Most Women," *Journal of Insurance Regulation*, Mar. 1988, vol. 6, No. 3, Publisher: National Association of Insurance Commissioners.

Butler, Patrick, "Why the Standard Automobile Insurance Market Breaks Down in Low-Income Zip Codes," *Report to the Texas House Committee on Insurance*, Apr. 6, 1999, Publisher: National Organization for Women.

Butler, Patrick, "Unmetered Premiums Subsidize Overuse of Automobile Transportation," *Contingencies: The Journal of the Actuarial Profession*, May 1990, vol. 2, No. 3, Publisher: American Academy of Actuaries.

Woll, Richard, "Why did the Texas Legislature pass the cents-per-mile choice law?" *Cents-Per-Mile Choice for Car Insurance*, Publisher: www.centspermilenow.org/faq.htm.

Baker, Dean, "Insurance By the Mile: A Simple Way to Slow Global Warming," *Center for Economic and Policy Research*, Jun. 1, 2006, Publisher: www.cepr.net.

Nerad, Jack R., "Insurance By the Mile," Publisher: www.antiquecar.com.

Author Unknown, "Developing Pay-Per-Mile Auto Insurance," www.clfventures.org/eia.html, Publisher: CLF Ventures.

Author Unknown, *Motorcycle News Community Forum*, Publisher: www.motorcyclenews.com.

Paul, Katherine J., "Advocating Mileage-Based Auto Insurance," *Conservation Matters—Spring 2003*, Publisher: www.clf.org/general/index.asp?id=493.

(56) References Cited

OTHER PUBLICATIONS

Author Unknown, "Technical Methods for Analyzing Pricing Measures to Reduce Transportation Emissions," EPA Publication No. EPA231-R-98-006, Aug. 1998, Publisher: U.S. Environmental Protection Agency.
Glover, Edward L. et al., "Trip Length Activity Factors for Running Loss and Exhaust Running Emissions," EPA Publication No. EPA420-R-01-013, Apr. 2001, Publisher: U.S. Environmental Protection Agency.
Beardsley, Megan, "Development of Speed Correction Cycles," EPA Publication No. EPA420-R-01-042, Jul. 2001, Publisher: U.S. Environmental Protection Agency.
Garman, Thomas, Pay-per-Mile Auto Insurance, 652 Essay for Garman's 8th, 2003.
Goch, Lynn, "Car Wars," *Best's Review*, Oct. 2000.
Goch, Lynn, "What Works Online," *Best's Review*, May 2002.
Goch, Lynn, "Gearing Up," *Best's Review*, Oct. 2003, pp. 20-24, 26, 28-30, 32, 34, 36.
Hagerbaumer, Christine, "Goodbye Gridlock: Improving the Way Oregon Funds Transportation," *A Report by the Oregon Environmental Council*, Apr. 2002, Publisher: Oregon Environmental Council.
McCutcheon, Chuck, "Buying Auto Insurance by the Mile," *The Grand Rapids Press*, Aug. 6, 2006.
Author Unknown, *US Insurance Industry I.I.I. Insurance Fact Book*, 2002, Publisher: Insurance Information Institute.
Butler, Patrick, "Insurance Department 'Catch 22' Shields Auto Insurers from Consumer Challenges," *Journal of Insurance Regulation*, Mar. 1989, pp. 285-289, vol. 7, No. 3, Publisher: National Association of Insurance Commissioners.
Jacklet, Ben, "'Pay as you drive' policies get boost," *Portland Tribune*, Jan. 10, 2003.
Leboeuf-Lamb, "State Insurance Legislation & Regulatory Developments: Dec. 13, 2001-Jan. 17, 2002," Jan. 2002, Publisher: www.llgm.com.
Litman, Todd, "Distance-Based Vehicle Insurance as a TDM Strategy," Mar. 24, 2003, pp. 1-26, Publisher: Victoria Transport Policy Institute.
Author Unknown, "Insurance Game Pits Men Against Women: Letter to the Editor," *The New York Times*, May 14, 1994.
Eisenberg, Ann, "What's Next: Paying for Car Insurance By the Mile," *The New York Times*, Apr. 20, 2000.
Green, Meg, "O Canada!" *Best's Review*, Oct. 2004.
Author Unknown, "Transportation Solutions," *Oregon Environmental Council Global Warming/Transportation Program*, Publisher: Oregon Environmental Council.
Panko, Ron, "Making a Dent in Auto Insurance Fraud," *Best's Review*, Oct. 2001.
Panko, Ron, "Beyond Repair," *Best's Review*, Oct. 2002.
Author Unknown, "What is Project XL?" www.epa.gov/projectxl/file2.htm.
Author Unknown, "Pay-As-You-Drive Insurance Bill Heads to House Floor," Press Release, Apr. 14, 2003.
Author Unknown, "House Passes 'Pay-As-You-Drive' Insurance Bill," Press Release, Apr. 23, 2003.
Author Unknown, "Oregon Passes First-of-its-kind Bill in Nation to Promote Pay-As-You-Drive' Auto Insurance," Press Release, Jun. 19, 2008.
Author Unknown, "Sense and Sustainability: Smart thinking to restart European transport policy," 2004, Publisher: European Federation for Transport and Environment.
Author Unknown, "New states show leadership in pricing for trucks," *T&E Bulletin No. 129*, Jun. 2004, Publisher: European Federation for Transport and Environment.
Author Unknown, "European Parliament steps towards getting transport's prices right," *T&E Press Release*, Apr. 21, 2004, Publisher: European Federation for Transport and Environment.
Author Unknown, "So what should you ask your potential MEP?" *T&E Bulletin Special Feature*, 2004, Publisher: European Federation for Transport and Environment.
Author Unknown, "MEPs Angry at Time Pressure on TENS Guidelines," *T&E Bulletin No. 125*, Feb. 2004, Publisher: European Federation for Transport and Environment.
Author Unknown, "News from the European Federation for Transport and Environment," *T&E Bulletin No. 126*, Mar. 2004, Publisher: European Federation for Transport and Environment.
Author Unknown, *T&E Bulletin No. 128*, May 2004, vol. 128, Publisher: European Federation for Transport and Environment.
Author Unknown, "Another three years to create 'green skies'," *T&E Bulletin No. 133*, Nov. 2004, Publisher: European Federation for Transport and Environment.
Author Unknown, "External Costs of Transport underestimated at 650 EUR billion," *T&E Bulletin No. 134*, Dec. 2004, Publisher: European Federation for Transport and Environment.
Author Unknown, "Comparative information on transport prices and taxation across Europe," Complied by T&E Brussels, Sep. 2000, Published at www.t-e.nu.
Author Unknown, *2004 Annual Report*, Publisher: Texas Department of Insurance.
Carlson, Thomas R. et al., "Development of Speed Correction Cycles Prepared by Sierra Research, Inc.," Jun. 26, 1997, Publisher: U.S. EPA Assessment and Modeling Division.
Author Unknown, "Value Pricing Pilot Program," www.fhwa.dot.gov/policy/opts/valuepricing.htm, , Publisher: Office of Transportation Policy Studies.
Author Unknown, "Vehicle Use Pricing," *Value Pricing Homepage*, Published at: www.valuepricing.org.
Author Unknown, "Online TDM Encyclopedia," www.vtpi.org/tdm/index.php, Publisher: Victoria Transport Policy Institute.
Author Unknown, "Our Approach to Problem Solving," www.vtpi.org/approach/index.php, Publisher: Victoria Transport Institute.
Author Unknown, "Weekly Car Guide: Aug. 13, 2004," Aug. 13, 2004, Publisher: www.thecarconnection.com.
Author Unknown, "What is Value Pricing?" *Value Pricing Homepage*, Publisher: www.valuepricing.org.
Wright, Jeff, "Insurance bill trades miles for cash," *Salem Register-Guard*, Apr. 23, 2003.
Author Unknown, "Pay As You Drive Insurance," www.orcouncil.org/Pollution/PAYD.htm; Publisher: Oregon Environmental Council.

* cited by examiner

METHOD FOR USING ELECTRONIC METADATA TO VERIFY INSURANCE CLAIMS

CROSS REFERENCE TO RELATED APPLICATIONS

This application claims priority to U.S. Provisional Patent Application No. 61/103,363 entitled "METHOD FOR USING ELECTRONIC METADATA TO VERIFY INSURANCE CLAIMS," filed Oct. 7, 2008, the contents of which are hereby incorporated by reference.

FIELD OF THE INVENTION

This disclosure relates to the provision of insurance products in general and, more specifically, to the use of metadata in electronic media to facilitate policy implementation.

BACKGROUND OF THE INVENTION

Insurance products, particularly automotive insurance, have become tailored to providing coverage more fitting to modern living habits. However, available technology has not always kept pace. More and more commerce is being done over the Internet, and even using mobile devices. Camera phones, smart phones, cell phones with texting and multimedia messaging ability, lightweight laptops, and so-called "nettop" devices allow for a reduced need to actually be present in order to communicate. Documents, photos, and other communications can be submitted from virtually anywhere. Many digital cameras also provide enhanced data with digital photos, such as global positioning system (GPS) coordinates.

Specific to the field of insurance is the need to accurately and efficiently verify facts related to claims and coverage. Economies of scale and improved efficiencies could be obtained from not actually having to physically inspect damaged property (e.g., automobiles or homes) when a claim arises. In the context of automobile insurance, simply avoiding physically sending a claims agent or adjuster to do a simple odometer reading or verify that the claim is legitimate could be a worthwhile goal—particularly as energy prices continue to increase. What is needed is a system and method for addressing the above and related issues.

SUMMARY OF THE INVENTION

The present invention disclosed and claimed herein, in one embodiment thereof, comprises a method for processing a digital media file. The method includes receiving a digital file from a customer, extracting metadata from the file, and verifying the metadata prior to accepting the digital file.

The method may also include verifying the representation of a physical token in the digital file. The physical token may be a barcode, a license plate, an identification card, or a state issued driver's license.

The invention of the present disclosure, in another embodiment, comprises a method of validating an insurance claim. The method includes receiving a request to make a claim from a customer, receiving a digital file, such a digital photograph, from the customer in association with the claim, and verifying that a representation of a required physical token appears in the digital file.

The physical token may be a barcode, a license plate, or a driver's license. The physical token may be provided to a customer following a request to make the insurance claim. It could be provided via the internet, or mobile phone network. The method may also include examining metadata of the digital file to determine if the digital file was created following provision of the physical token to the customer.

The invention of the present disclosure, in embodiment, comprises a computer readable media having computer readable instructions thereon. The instructions comprise instructions for receiving a digital file, extracting metadata from the file, determining the date of creation of the digital file from the metadata, comparing the date of creation of the digital file to a predetermined date range associated with an insurance policy, and accepting the file if the date of creation is within the predetermined range. A computer user may be informed of the rejection of the file if the date of creation is not within the predetermined range.

The computer user may be an insurance customer, or insurance agent. The computer readable media may also comprise instructions for providing a physical token to a user. The physical token may be a barcode.

DETAILED DESCRIPTION OF THE PREFERRED EMBODIMENTS

Digital media files often contain what is referred to as metadata. In the case of a digital photograph, this may include the date and time the photo was taken, the type of camera, the camera settings, camera orientation, and even location coordinates (such as GPS). Even photos or videos taken with mobile devices may contain metadata.

In the insurance industry, digital media, such as digital photos or video, may be used to document certain facts or events. For example, when coverage is provided for an automobile, an insurer may wish to obtain one or more photographs of the vehicle to document that the vehicle is the proper make, model, etc., as reported by the customer, and to document any preexisting faults or damage. In the present disclosure, examples given relate to the provision of automobile insurance, but it is understood that the same systems and methods may be applicable to other enterprises (e.g., home owners insurance).

Figure 1:
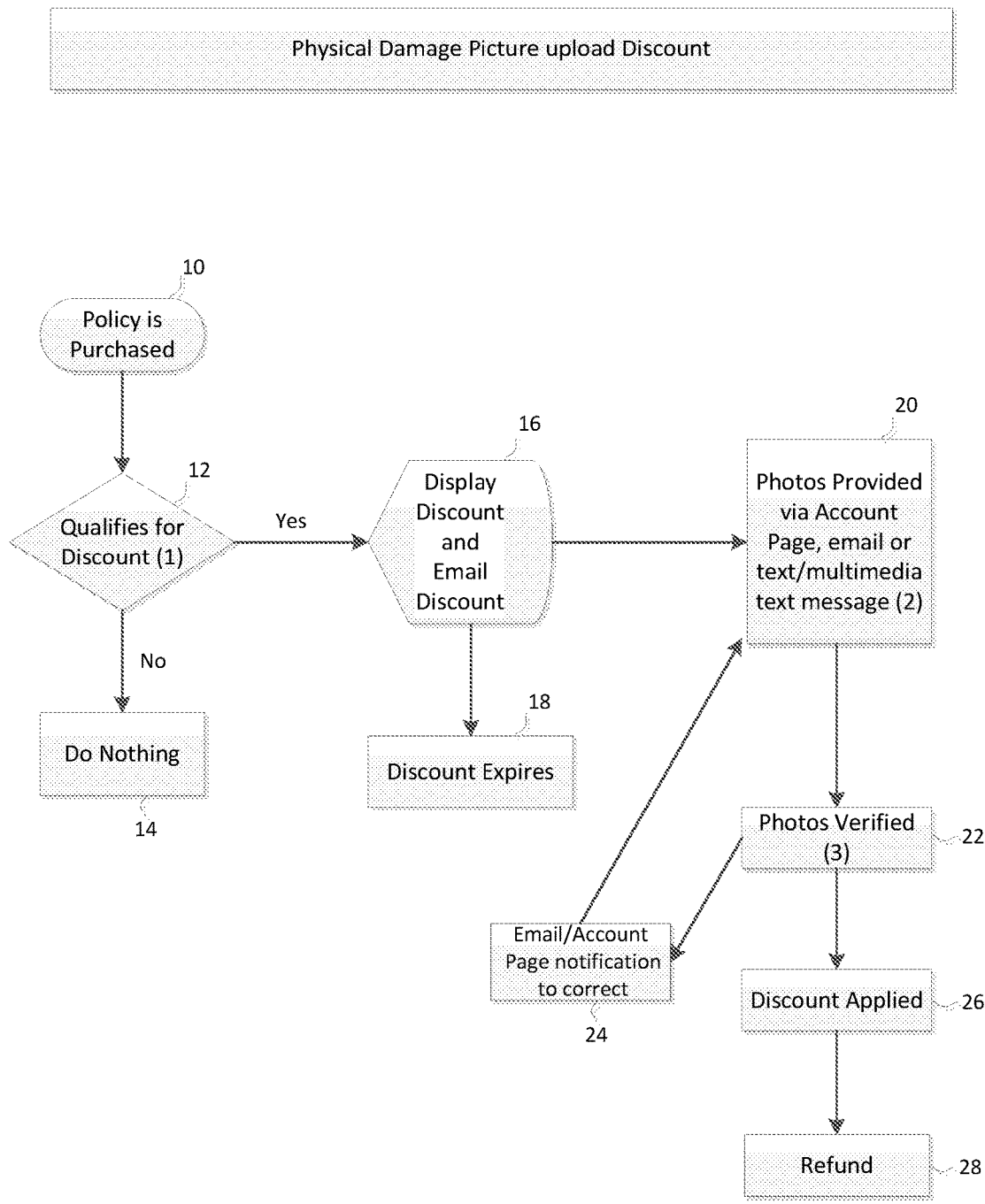
FIG. 1 is a flow diagram illustrating a process for providing a baseline digital file for use in association with an insurance policy.

Referring now to FIG. 1, a flow diagram illustrating a process for providing a baseline digital file for use in association with an insurance policy is shown. In the present example, a customer will receive a discount for providing a digital photo of an automobile when an insurance policy is purchased or renewed at step 10. A determination may be made as to whether the current policy provides for a discount upon the provision of a digital photo. This occurs at step 12. In the present example, the insurance policy must be one that provides physical damage coverage, and the customer must have selected this coverage when initiating or renewing the policy. If the current policy does not provide for a discount for provision of a digital photo, it is not offered, as reflected at step 14.

If a discount is available, it will be offered to the customer at step 16. In the present embodiment, the details relating to the discount may be displayed on a view screen, emailed to the customer, or provided via mobile phone (e.g., via text or multimedia message). In the present example, it is assumed that the insurance customer is dealing directly with the insurer via the internet. The customer may be able to purchase policies and/or interact with the insurance company via a secure website, for example. However, it is understood that aspects of the present disclosure may also be applicable where the insured purchases a policy through an agent. For example, a customer may purchase a policy through an agent who then communicates via email or the web to allow the photo to be uploaded.

At step 16, the details of the discount offer may be provided. For example, the deadline for receiving the digital photo and discount may be provided. Requirements for the photo itself may also be provided and may include minimum resolution, color quality, lighting conditions, viewpoints, and other requirements. If the discount is allowed to expire, the method ends at step 18.

At step 20, the digital photo or photos required for the discount are provided to the insurer. The photos may be uploaded through a secure webpage (e.g., a customer account page). In another embodiment, a unique email address may be provided that is associated with the corresponding customer account. This address may be used to allow the customer to send the photos via email attachment. In yet another embodiment, a unique address or number may be associated with the customer account for receiving multimedia phone messages. Photos taken with a camera phone or otherwise located on the phone may be sent to the specified number or address. Rather than a unique email address or number, multiple customers could be given the same email or number and the originating email address or phone number could be used to properly associate the received files with the correct customer account.

Upon receiving the digital photos, they will be verified or tested for validity at step 22. In the present embodiment, a combination of manual and automated verification will be used. During an automated testing, the metadata embedded in the digital file may be automatically examined. This may occur on the server that received the photo, or another general purpose or dedicated computer. The metadata may be examined to determine if the photos are recent enough to be utilized. Other metadata parameters that can be checked include, but are not limited to, the resolution of the photo and whether the photo is a proper color photo.

Following an automated check, a manual check may be performed by a live person. For example, a check to make sure the vehicle is of the type, color, model, year, etc., as represented by the customer may be performed. Where a photo is provided or required that shows the automobile license plate, a check may be performed against public records to verify that the license plate shown is assigned to a vehicle of the type indicated by the customer. In one embodiment optical character recognition (OCR) or other automated verification means may be used to established the license plate number or presence of another token (as described below). This can also be verified by a person. Finally, the metadata that was automatically extracted can be examined manually if desired.

If the photo or photos fail automated and/or manual verification, a notice can be send to the customer at step 24. This may be by email, telephone, and/or through a status update on a customer account webpage. In some embodiments, the customer may be given a chance to provide corrected photos and the method returns to step 20. If the photos pass verification at step 22, the discount is applied at step 26. This discount could appear as a credit on the customer account, or could be processed as a refund at step 28.

It will be appreciated that the above described exemplary systems and methods could be adapted to be utilized if an insurer were to require a photo or other digital media file as a prerequisite for coverage. The system and method could also be adapted to provide for an immediate discount upon providing a digital media file rather than issuing a refund. A discount could also be provided that would be reversed if the required digital file were not received within a certain deadline. Thus, in various embodiments, a photo or other digital media file could be required by the insurer and either provided immediately by the customer, or allowed to be delivered in time-delayed fashion. Similarly, delivery of the file could be optional (with or without a discount) and delivered immediately, or time delayed.

In some cases, an odometer reading of a covered vehicle may be needed by an insurance provider. This may be to verify that the vehicle is still covered under an insurance policy, or to verify a final reading when a policy is cancelled or renewed. In some cases, a photograph of the odometer may suffice. Here again, digital cameras or camera phones may be used to provide the photograph of the current odometer reading.

Figure 2:
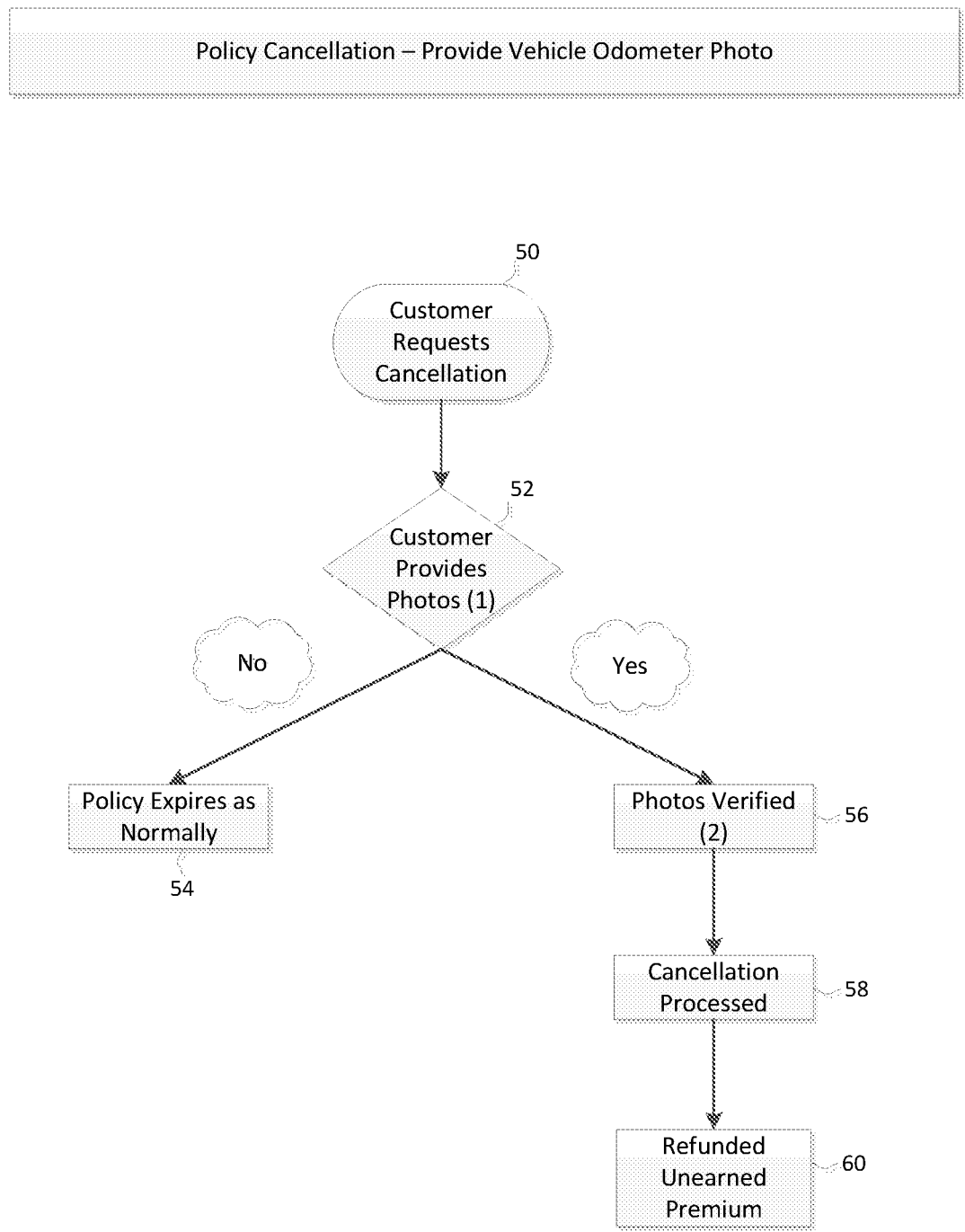
FIG. 2 is a flow diagram illustrating a process for receiving a digital file for verification of an odometer reading.

Referring now to FIG. 2, a flow diagram illustrating a process for receiving a digital file for verification of an odometer reading is shown. The present example assumes that the odometer reading is for the purposes of an insurance policy cancellation, but other uses of photographs of odometers readings are contemplated. At step 50, the customer requests cancellation. This may be via email, customer webpage, or interaction with an insurance specialist. The customer may be informed of the option to provide a photo of an odometer reading at this point.

At step 52, the customer may provide photos. As described previously, the photo may be provided through a variety of means. A secure customer webpage, a unique email address, and/or a unique multimedia message address are all contemplated. At step 54, if no photos are provided, the policy is allowed to expire normally (e.g., without the return of unearned premium). However, if photos are provided, they may be verified at step 56.

Verification of the photos may be automated, manual, or a combination of the two. In one embodiment, the metadata of the photo will be examined. From the metadata the date of the photo and other information may be obtained. In the case of an odometer reading, only readings less than a certain age, or occurring on a certain date may be accepted. The actual figure on the odometer in the photo may be verified manually (e.g., by a person) to ensure the reading reflects what was reported by the customer. The date retrieved automatically from the metadata may also be manually verified.

At step 58, the cancellation is processed. This may result in a refund of unearned premium, based on the previously provided odometer reading, at step 60.

Any time a photo or other digital media file is provided to the insurer (for example, as discussed with respect to FIGS. 1 and 2) a physical token may be required to validate, or assist in validating, the photo. The physical token may be required to appear in at least one of the photos with the home or car that is the subject of the claim. In some embodiments, the token or tokens are not provided until actually needed. It could be provided only when the photo or other digital media file was requested. In this manner, only a current photo could be used since the customer would not have previously had access to the required token. These steps may reduce the possibility of fraud on the insurer.

The token might be a barcode or unique serial number or image. In another embodiment, a state issued driver's license, passport, or other official identification could serve as the physical token. In yet embodiment, the license plate of an insured automobile may serve as the required token.

Through publicly available data, in some states it is possible to verify that a license plate appearing in a photo actually corresponds to the insured automobile and/or driver. The insured may be required to make sure that the license plate appears or other physical token clearly in one or more of the photos. The license plate could also be combined with an additional token for additional measures of security (e.g., multiple tokens can be used).

In the case of a barcode being used as a physical token, it may be provided to the customer at the inception of an insurance policy or when a photograph is needed to verify a claim, odometer reading, or other event. In some embodiments, the bar code or other token may appear on the insurance verification card. The token could also be provided via mail, email, website, or multimedia message to a mobile device such as a cell phone. If the token is provided to a cell phone, smart phone, personal digital assistant (PDA), portable computer, or other portable device, the receiving device may provide a high enough resolution in displaying the token so as to be able to display the token on screen and appear in the photograph along with the covered automobile. In other cases (for example, where the cell phone also serves as the camera), the token may have to be produced on a printout.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A computer implemented method for processing a digital media file, the method comprising:
   specifying, by a server, a physical token associated with a customer upon receiving a request, via network communications with a computing device, for the purchase or cancellation of an insurance policy associated with the customer;
   receiving, at the server, (i) a digital photograph file from the computing device that is representative of an image of an insurance-related subject associated with the insurance policy, and (ii) an image of the physical token;
   electronically extracting, by the server, metadata embedded in the digital photograph file to provide extracted metadata;
   analyzing, by the server, the extracted metadata to determine that the digital photograph file has an image resolution exceeding a minimum resolution;
   determining, by the server, a date that the digital photograph file was captured based upon the extracted metadata;
   determining, by the server, whether the date when the digital photograph file was captured is within a predetermined date range;
   performing, by the server, an automated image recognition process to determine whether the physical token is contained within the image of the insurance-related subject, wherein the automated image recognition process includes using optical character recognition (OCR) to detect a presence of the physical token in the image of the insurance-related subject;
   verifying, by the server, the digital photograph file when it is determined that (i) the digital photograph file was captured within the predetermined date range, and (ii) the physical token is contained within the image of the insurance-related subject; and
   in response to the verification of the digital photograph file and the analysis of the extracted metadata, applying a discount or refund to an insurance policy in accordance with the received request for the purchase or cancellation of the insurance policy.

2. The method of claim 1, wherein the physical token is a barcode.

3. The method of claim 1, wherein the physical token is a license plate.

4. The method of claim 1, wherein the physical token is an identification card.

5. The method of claim 1, wherein the physical token is a state issued driver's license.

6. A computer implemented method of validating an insurance claim, the method comprising:
   receiving, at a server, a request to make an insurance claim via communications with a computing device for a loss associated with an insurance-related subject covered by an insurance policy;
   specifying, by the server, a physical token that is required to appear in a digital photograph of the insurance-related subject when the insurance claim is received;
   receiving, by the server, a digital photograph of the insurance-related subject from the computing device in association with the received insurance claim;
   analyzing, by the server, embedded metadata of the digital photograph to determine that the digital photograph has an image resolution exceeding a minimum resolution; and
   performing, by the server, an automated image recognition process on the digital photograph to verify that the physical token appears in the digital photograph of the insurance-related subject associated with the received insurance claim,
   wherein the automated image recognition process includes using optical character recognition (OCR) to detect a presence of the physical token in the digital photograph of the insurance-related subject, and
   wherein the verification of the digital photograph and the analysis of the embedded metadata are conditions that are satisfied prior to the server processing the insurance claim.

7. The method of claim 6, wherein the physical token is a barcode.

8. The method of claim 6, wherein the physical token is a license plate.

9. The method of claim 6, wherein the physical token is a driver's license.

10. The method of claim 6, further comprising examining the embedded metadata of the digital photograph to determine if the digital photograph was created following the provision of the specified physical token to the customer.

11. The method of claim 6, wherein the physical token is provided to the customer via the internet.

12. The method of claim 6, wherein the physical token is provided to the customer via mobile phone network.

13. A computer system comprising:
one or more computer processors for executing computer instructions, and
a non-transitory tangible computer-readable medium storing the computer instructions thereon, which, when executed by the one or more processors, cause the one or more processors to:
- receive a request via communications with a computing device for the purchase or cancellation of an insurance policy associated with a customer;
- receive a digital photograph file from the computing device including a date specified in metadata embedded in the digital photograph file;
- extract the embedded metadata from the digital photograph file to provide extracted metadata;
- analyze the extracted metadata of the digital photograph file to determine that the digital photograph file has an image resolution exceeding a minimum resolution;
- determine the date when the digital photograph file was captured based upon the embedded metadata;
- compare the date that the digital photograph file was captured to a predetermined date range;
- perform an automated image recognition process that includes using optical character recognition (OCR) to detect a presence of the physical token in an image included in the digital photograph file;
- accept the digital photograph file if (i) the date that the digital photograph file was captured is within the predetermined range (ii) the image resolution exceeds the minimum resolution, and (iii) the presence of the physical token is detected in the image; and
- in response to accepting the digital photograph file, apply a discount or refund, respectively, in accordance with the received request for the purchase or cancellation of the insurance policy associated with the customer.

14. The computer system of claim 13, wherein the computer user is an insurance customer.

15. The computer system of claim 13, wherein the computer user is an insurance agent.

16. A computer system comprising:
one or more computer processors for executing computer instructions, and;
a non-transitory tangible computer-readable medium storing the computer instructions thereon, which when executed by the one or more processors, cause the one or more processors to:
- receive a request from communications with a computing device to make an insurance claim for a loss associated with an insurance-related subject covered by an insurance policy;
- specify a physical token that is required to appear in a digital photograph of the insurance-related subject when the insurance claim is received;
- receive a digital photograph of the insurance-related subject from the computing device in association with the received insurance claim;
- analyze embedded metadata of the digital photograph to determine that the digital photograph has an image resolution exceeding a minimum resolution; and
- perform an automated image recognition process to the digital photograph to verify the digital photograph by determining that the physical token appears in the digital photograph of the insurance-related subject associated with the received insurance claim,
- wherein the automated image recognition process includes using optical character recognition (OCR) to detect a presence of the physical token in the digital photograph of the insurance-related subject, and
- wherein the verification of the digital photograph and the analysis of the embedded metadata are conditions that are satisfied prior to the one or more computer processors processing the insurance claim.

* * * * *